United States Patent [19]

Uchiyama et al.

[11] Patent Number: 5,608,021

[45] Date of Patent: Mar. 4, 1997

[54] CATIONIC POLYMER THICKENER AND PROCESS FOR PREPARING THE SAME

[75] Inventors: Yujiro Uchiyama, Osaka; Junichi Matsumoto, Kashiwara; Yoshihiro Okuda, Higashiosaka, all of Japan

[73] Assignee: Osaka Yuki Kagaku Kogyo Kabushiki Kaisha, Osaka, Japan

[21] Appl. No.: 420,668

[22] Filed: Apr. 12, 1995

Related U.S. Application Data

[63] Continuation-in-part of Ser. No. 255,729, Jun. 7, 1994, abandoned, which is a continuation-in-part of Ser. No. 158,284, Nov. 29, 1993, abandoned.

[51] Int. Cl.$^6$ ............................ A61K 7/075; C08F 2/06
[52] U.S. Cl. ........................ 526/210; 526/264; 526/265; 424/70.15; 424/70.17
[58] Field of Search ............................ 424/78.18, 70.15, 424/70.16, 78.1; 526/210, 264

[56] References Cited

U.S. PATENT DOCUMENTS

| | | | |
|---|---|---|---|
| 4,030,512 | 6/1977 | Papantoniou et al. | 424/70.11 |
| 4,521,404 | 6/1985 | Lorenz et al. | 424/71 |
| 4,524,175 | 9/1985 | Fink et al. | 524/516 |
| 5,126,124 | 6/1992 | Tazi et al. | 424/47 |
| 5,208,014 | 5/1993 | Dubief et al. | 424/71 |
| 5,296,218 | 3/1994 | Chen et al. | 424/71 |
| 5,321,110 | 6/1994 | Shih | 526/264 |

FOREIGN PATENT DOCUMENTS

| | | |
|---|---|---|
| 0055801 | 7/1982 | European Pat. Off. . |
| 0201342 | 12/1986 | European Pat. Off. . |
| 5-721210 | 12/1982 | Japan . |
| 4-106114 | 4/1992 | Japan . |
| 4-108715 | 4/1992 | Japan . |

*Primary Examiner*—Peter F. Kulkosky
*Attorney, Agent, or Firm*—Varndell Legal Group

[57] ABSTRACT

Cationic thickener prepared by polymerizing a monomer composition comprising 15 to 85% by weight of at least one of acrylic monomer having an amino group and methacrylic monomer having an amino group, 20 to 80% by weight of vinyl monomer, 1 to 20% by weight of monomer having at least one of acryloyl group and methacryloyl group and 0.1 to 20% by weight of crosslinkable vinyl monomer, and a process for preparing the same. This cationic thickener contains little impurities, and can be easily mixed with a cationic polymer for setting, and forms a flexible film after drying.

8 Claims, No Drawings

CATIONIC POLYMER THICKENER AND PROCESS FOR PREPARING THE SAME

CROSS-REFERENCE TO RELATED APPLICATION

This is a continuation-in-part of application Ser. No. 255,729, now abandoned, filed on Jun. 7, 1994, which is a continuation-in-part of application Ser. No. 158,284, now abandoned, filed on Nov. 29, 1993.

BACKGROUND OF THE INVENTION

The present invention relates to a cationic thickener and a process for preparing the same, and more particularly to a cationic thickener which can be suitably used in, for instance, cosmetics, fragrant agents and the like, and a process for preparing the same.

Conventionally base gels have been investigated, and there have been known base gels comprising a salt prepared by neutralizing a crosslinked polyacrylic acid with an alkaline material as disclosed in Japanese Examined Patent Publication No. 4141/1957, Japanese Unexamined Patent Publication No. 46586/1976.

However, since those base gels have —COOH groups in their molecules, and their main structures are composed of anionic polymers prepared by neutralizing all or a part of the —COOH groups with NaOH, KOH, amine or the like, it is difficult to add raw materials for cosmetics for hair and scalp such as a cationic polymer for setting to the base gels. For instance, when a cationic polymer for setting having a quarternary amine in its molecule is added to the base gel, neutralization of electric charge occurs between the anionic polymer and the cationic polymer for setting, and thereby coagulation, cloudiness, turbidity and the like are sometimes caused.

Accordingly, polymers for setting which can be added to the anionic base gel (anionic polymer) are only nonionic polymers for setting such as polyvinylpyrrolidone and vinylpyrrolidone-vinyl acetate copolymer, and anionic polymers for setting represented by an alkanolamine solution of an acrylic resin.

Also, since an aqueous cosmetic composition containing the base gel forms a hard film after drying, when the aqueous cosmetic composition is used as, for instance, cosmetic composition for hair setting, peeling the film from hair, that is, flaking phenomenon occurs. Therefore, the use of the aqueous cosmetic composition has been limited.

On the other hand, as a base gel which forms a soft and flexible film after drying, there is known a base gel which is prepared by carrying out an aqueous emulsion polymerization of a crosslinkable base monomer having an amino group and then adjusting a pH value to increase its viscosity (Japanese Unexamined Patent Publication No. 133145/1982). However, since the crosslinkable base monomer is easily hydrolyzed, when the crosslinkable base monomer is hydrolyzed and then neutralized by an acid treatment, a cationic group is introduced into the crosslinkable base monomer. As a result, since an anionic group and a cationic group coexist in the same molecular chain of an obtained polymer, the polymer sometimes does not become uniform.

Also, when N,N-dimethylaminoethyl methacrylate is used as a raw material of the base gel described above, a desirable polymer cannot be obtained since hydrolysis is caused with violence during the polymerization reaction. In other words, this fact means that there cannot be used N,N-dimethylaminoethyl methacrylate which is widely and industrially used and known as a raw material for cosmetics having excellent properties, and that there is inconvenience in the selection of the starting monomer for the base gel. Also, there is a defect that the contamination with an impurity such as a surface active agent cannot be avoided in all of emulsion polymerizations.

U.S. Pat. No. 4,542,175 discloses a method of thickening an aqueous system containing an aqueous dispersion of a polymer comprising (A) 20 to 100% by weight of a basic unsaturated free radically polymerizable monomer having at least one basic nitrogen atom, (B) 0 to 95% by weight of a neutral unsaturated free radically polymerizable comonomer and 0 to 30% by weight of a neutral unsaturated free radically polymerizable comonomer, which is prepared by aqueous emulsion polymerization. However, a dialkylaminoalkyl (meth)acrylate having a short alkyl group like N,N-dimethylaminoethyl methacrylate cannot be used as one of the components for the polymer since the dialkylaminoalkyl (meth)acrylate is easily hydrolyzed during its polymerization reaction in water. Moreover, there are some defects such that impurities such as a surface active agent are contained in the resulting aqueous dispersion of the polymer, and that the polymer does not become uniform.

In order to solve the above problems, there is proposed a gel made of a copolymer prepared by copolymerizing a (meth)acrylic acid ester such as N,N-dimethylaminoethyl acrylate, an oxyalkylene di(meth)acrylate and a vinyl moonomer such as N-vinylpyrrolidone as disclosed in Japanese Unexamined Patent Publication No. 106114/1992. However, the gel is not good in flexibility and gloss of its formed film.

It is an object of the present invention to provide a cationic thickener which can be blended with a cationic polymer for setting.

It is a further object of the present invention to provide a cationic thickener which forms a flexible film after drying.

It is a still further object of the present invention to provide a cationic thickener containing little impurities.

It is a still further object of the present invention to provide a cationic thickener having excellent compatibility with a nonionic resin, a cationic resin and an amphoteric resin as well as water.

It is a still further object of the present invention to provide a cationic thickener having a high gel viscosity.

These and other objects of the present invention will become apparent from the description hereinafter.

SUMMARY OF THE INVENTION

In accordance with the present invention, there is provided a cationic thickener prepared in a nonaqueous system in the absence of a surface active agent by polymerizing a monomer composition containing (A) 15 to 85% by weight of at least one of an acrylic monomer having an amino group and a methacrylic monomer having an amino group represented by the general formula (I):

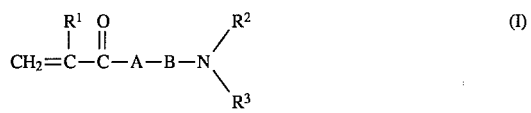

wherein $R^1$ is hydrogen atom or methyl group, each of $R^2$ and $R^3$ is independently hydrogen atom, methyl group, ethyl group or t-butyl group, A is oxygen atom or —NH— group, and B is a linear or branched alkylene group having 1 to 4 carbon atoms, (B) 20 to 80% by weight of a vinyl monomer represented by the general formula (II):

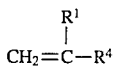  (II)

wherein $R^1$ is as defined above and $R^4$ is a group represented by the general formula:

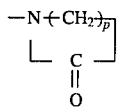

wherein p is 3 or 4, or a group represented by the general formula:

(C) 1 to 20% by weight of at least one of a monomer having acryloyl group and a monomer having methacryloyl group represented by the general formula (III):

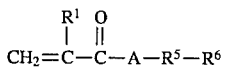  (III)

wherein $R^1$ and A are as defined above, $R^5$ is a linear or branched alkylene group having 1 to 17 carbon atoms, a group represented by the general formula (IV):

  (IV)

wherein q is an integer of 1 to 25 or a group represented by the general formula (V):

  (V)

wherein r is an integer of 1 to 25, and $R^6$ is hydrogen atom or methyl group, and (D) 0.1 to 20% by weight of a crosslinkable vinyl monomer.

Also, in accordance with the present invention, there is provided a process for preparing a cationic thickener comprising the steps of:

polymerizing in a nonaqueous system in the absence of a surface active agent, a monomer composition comprising (A) 15 to 85% by weight of at least one of an acrylic monomer having an amino group and a methacrylic monomer having an aminio group represented by the general formula (I):

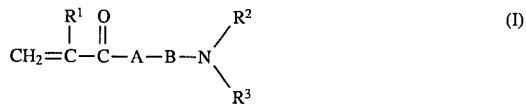  (I)

wherein $R^1$ is hydrogen atom or methyl group, each of $R^2$ and $R^3$ is independently hydrogen atom, methyl group, ethyl group or t-butyl group, A is oxygen atom or —NH— group, and B is a linear or branched alkylene group having 1 to 4 carbon atoms, (B) 20 to 80% by weight of a vinyl monomer represented by the general formula (II):

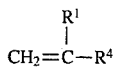  (II)

wherein $R^1$ is as defined above and $R^4$ is a group represented by the general formula:

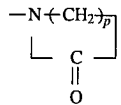

wherein p is 3 or 4, or a group represented by the general formula:

(C) 1 to 20% by weight of at least one of a monomer having acryloyl group and a monomer having methacryloyl group represented by the general formula (III):

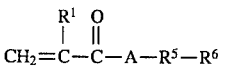  (III)

wherein $R^1$ and A are as defined above, $R^5$ is a linear or branched alkylene group having 1 to 17 carbon atoms, a group represented by the general formula (IV):

  (IV)

wherein q is an integer of 1 to 25 or a group represented by the general formula (V):

  (V)

wherein r is an integer of 1 to 25, and $R^6$ is hydrogen atom or methyl group, and (D) 0.1 to 20% by weight of a crosslinkable vinyl monomer with heating in a nonaqueous solvent under an atmosphere of inert gas; and removing a solvent from an obtained reaction solution to give powder.

DETAILED DESCRIPTION

As mentioned above, the cationic thickener of the present invention comprises the components of (A) 15 to 85% by weight of at least one of an acrylic monomer having an amino group and a methacrylic monomer having an amino group represented by the general formula (I):

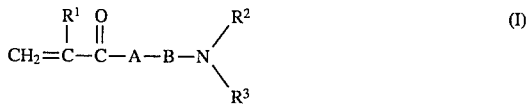  (I)

wherein $R^1$ is hydrogen atom or methyl group, each of $R^2$ and $R^3$ is independently hydrogen atom, methyl group, ethyl group or t-butyl group, A is oxygen atom or —NH— group and B is a linear or branched alkylene group having 1 to 4 carbon atoms, (B) 20 to 80% by weight of a vinyl moonomer represented by the general formula (II):

$$CH_2=C-R^4 \quad \text{(II)}$$
$$\overset{|}{R^1}$$

wherein $R^1$ is as defined above and $R^4$ is a group represented by the general formula:

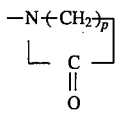

wherein p is 3 or 4, or a group represented by the general formula:

$$-\overset{O}{\underset{\|}{C}}-NH_2,$$

(C) 1 to 20% by weight of at least one of a monomer having acryloyl group and a monomer having methacryloyl group represented by the general formula (III):

$$CH_2=\overset{R^1}{\underset{|}{C}}-\overset{O}{\underset{\|}{C}}-A-R^5-R^6 \quad \text{(III)}$$

wherein $R^1$ and A are as defined above, $R^5$ is a linear or branched alkylene group having 1 to 17 carbon atoms, a group represented by the general formula (IV):

$$-(C_2H_4O)_{\overline{q}} \quad \text{(IV)}$$

wherein q is an integer of 1 to 25 or a group represented by the general formula (V):

$$-(C_3H_4O)_{\overline{r}} \quad \text{(V)}$$

wherein r is an integer of 1 to 25, and $R^5$ is hydrogen atom or methyl group, and (D) 0.1 to 20% by weight of a crosslinkable vinyl monomer.

Since least one of the acrylic monomer having an amino group and the methacrylic monomer having an amino group [hereinafter referred to as "(meth)acrylic monomer having an amino group"] represented by the general formula (I) is used in the present invention, properties of an electrolyte are imparted to an obtained copolymer when the copolymer is neutralized with an adequate acid.

Typical examples of the (meth)acrylic monomer having an amino group are, for instance, (meth)acrylates such as N,N-dimethylaminoethyl (meth)acrylate, N,N-diethylaminoethyl (meth) acrylate and N,N-dimethylaminopropyl (meth)acrylate; (meth)acrylamides such as N,N-dimethylaminoethyl (meth)acrylamide, N,N-diethylaminoethyl (meth) acrylamide and N,N-dimethylaminopropyl (meth)acrylamide, and the like, and the present invention is not limited to the exemplified ones. In the present invention, those (meth)acrylic monomers having an amino group can be used alone or in an admixture thereof.

The content of the (meth)acrylic monomer having an amino group in the moonomer composition is adjusted so as to become 15 to 85% by weight. When the content of the (meth)acrylic monomer having an amino group is less than 15% by weight, the content of the (meth)acrylic monomer having an amino group to be neutralized later with an acid becomes too low and a cationic thickener having a sufficient gel viscosity cannot be easily obtained. When the content of the (meth)acrylic monomer having an amino group is more than 85% by weight, a film formed by drying the cationic thickener loses its flexibility.

The vinyl monomer represented by the general formula (II) is used to impart flexibility, gloss and smoothness to a film formed from the cationic thickener.

Typical examples of the vinyl monomer are, for instance, N-vinylpiperidone, N-vinylpyrrolidone, acrylamide, methacrylamide and the like, and the present invention is not limited to the exemplified ones. In the present invention, the vinyl monomer can be used alone or in an admixture thereof.

The content of the vinyl monomer in the monomer composition is adjusted so as to become 20 to 80% by weight, preferably 20 to 60% by weight, more preferably 40 to 60% by weight. When the content of the vinyl monomer is more than 80% by weight, the gel viscosity of an obtained cationic thickener is remarkably lowered. When the content of the vinyl monomer in the monomer composition is less than 20% by weight, flexibility, gloss and smoothness would not be sufficiently imparted to a film formed from the cationic thickener.

In the present invention, at least one of the monomer having acryloyl group and the monomer having methacryloyl group [hereinafter referred to as "monomer having (meth)acryloyl group"] represented by the general formula (III) is used. When the monomer having (meth)acryloyl group is used in the cationic thickener, excellent improvement of gloss of a film formed from the cationic thickener and high compatibility with various resins for setting can be accomplished.

Concrete examples of the monomer having (meth)acryloyl group are, for instance, methyl (meth)acrylate, ethyl (meth)acrylate, propyl (meth)acrylate, butyl (meth)acrylate, hexyl (meth) acrylate, octyl (meth)acrylate, lauryl (meth)acrylate, tridecyl (meth)acrylate, stearyl (meth)acrylate, cyclohexyl (meth)acrylate, N-t-butyl (meth)acrylamide, N-t-octyl (meth)acrylamide, N-methyl (meth)acrylamide, hydroxyethyl (meth)acrylate, hydroxypropyl (meth)acrylate, polyoxyethylene (meth)acrylate represented by the general formula (IV) in which q is an integer of 2 to 25, methoxypolyethylene glycol (meth)acrylate represented by the general formula (IV) in which q is an integer of 2 to 25, polypropylene glycol (meth)acrylate represented by the general formula (V) in which r is an integer of 2 to 25, methoxypolypropylene glycol (meth)acrylate represented by the general formula (V) in which r is an integer of 2 to 25 and the like, and the present invention is not limited to the exemplified ones. In the present invention, the monomer having (meth)acryloyl group can be used alone or in an admixture thereof.

In the general formula (III), it is desired that $R^5$ is a linear or branched alkylene group having 1 to 17 carbon atoms, preferably 8 to 17 carbon atoms and more preferably 12 to 17 carbon atoms in order to remarkably improve compatibility with cationic, nonionic and amphoteric polymers for setting, and to increase a gel viscosity.

The content of the monomer having (meth)acryloyl group in the monomer composition is adjusted so as to be 1 to 20% by weight, preferably 2 to 15% by weight. When the content of the monomer having (meth)acryloyl group is more than 20% by weight, the content of the hydrophobic groups contained in an obtained copolymer becomes high and water solubility is lowered even after the neutralization of the obtained copolymer, and thereby a smooth gel cannot be easily obtained. When the content of the monomer having (meth)acryloyl group is less than 1% by weight, since the gel viscosity is lowered, there is a necessity to increase the mount of the cationic thickener and the usable mount of various resins for setting is lowered and at the same time the gloss of a film formed from the cationic thickener after drying is lowered.

The crosslinkable vinyl monomer is one of essential components used in the monomer composition. If the crosslinkable vinyl monomer is not used in the monomer composition, an intended cationic thickener cannot be obtained.

The crosslinkable vinyl monomer has at least two carbon-carbon unsaturated double bonds in its molecule and is crosslinked with the other monomer.

Typical examples of the crosslinkable vinyl monomer are, for instance, acrylic monomers and methacrylic monomers having at least two carbon-carbon unsaturated double bonds in its molecule such as poly( meth )acrylic monomers such as ethyleneglycol di(meth)acrylate, polyoxyethylene di(meth)acrylate, polypropyleneglycol di(meth)acrylate, 1,2-ethanediyl di(meth)acrylate, 1,10-decanediyl di(meth)acrylate, trimethylolpropane tri(meth)acrylate, pentaerythritol tri(meth)acrylate, trimethylolethane tri(meth)acrylate, trimethylolpropane triglycidyl tri(meth)acrylate and tetramethylolmethane tetra(meth)acrylate; poly(meth)acrylamide monomers such as methylene-bis(meth)acrylamide, 1,2-bis(meth)acrylamidoethane, 1,5-bis( meth)acrylamidopentane, 1,10-bis(meth)acrylamidododecane and 1,1-bis(meth)acrylamido-1-phenylethane; vinyl monomers such as di vinyl benzene, 1,2-bis(p-vinylphenyl)ethane, 1,3-bis(p-vinylphenyl)propane and 1,4-bis(p-vinylphenyl)butane; and the like, and the present invention is not limited to the exemplified ones. In the present invention, the above-mentioned crosslinkable vinyl monomer can be used alone or in an admixture thereof.

The content of the crosslinkable vinyl monomer in the monomer composition is adjusted so as to be 0.1 to 20% by weight, preferably 1 to 10% by weight. When the content of the crosslinkable vinyl monomer is less than 0.1% by weight, crosslinking density of an obtained cationic thickener becomes too low, and therefore, the viscosity of the cationic thickener cannot be heightened. When the content of the crosslinkable vinyl monomer is more than 20% by weight, the viscosity of the cationic thickener becomes high, but fine aggregates are generated in the gel.

The cationic thickener is obtained by polymerizing the monomer composition containing the (meth)acrylic monomer having an amino group, the vinyl monomer, the monomer having (meth)acryloyl group and the crosslinkable vinyl monomer while, for instance, heating the monomer composition in a nonaqueous solvent in the absence of a surface active agent under an atmosphere of inert gas such as nitrogen gas; and by removing the solvent from the obtained reaction solution.

The polymerization reaction of the monomer composition can be carried out by solution polymerization method, bulk polymerization method or extraction polymerization method which is usually employed when a powdery product is obtained. The extraction polymerization can be easily carried out in a nonaqueous system in the absence of a surface active agent by polymerizing the monomer composition using a mixture of a good solvent and a bad solvent to precipitate an obtained copolymer from the polymerization solution as explained below.

In the present invention, the reason why the polymerization reaction is carried out in the nonaqueous solvent under an atmosphere of inert gas is that hydrolysis of ester groups existed in these monomers or an obtained copolymer is avoided. Also, the reason why a surface active agent is not used is that a uniform gel not containing impurities such as the surface active agent can be obtained when the surface active agent is not used.

In the present invention, as the nonaqueous solvent, a good solvent solely, or a mixture of the good solvent and a bad solvent is preferably used.

In the present invention, the good solvent is used in order to inhibit the generation of homopolymers caused by the difference of reactivity between each monomer and prepare a uniform copolymer.

In the present specification, the good solvent is intended to refer to a solvent which shows no turbidity when at least 20 g of a copolymer having a molecular weight of at least 10.000, which is prepared by copolymerizing the (meth-)acrylic monomer having an amino group represented by the general formula (I), the vinyl monomer represented by the general formula (II), the monomer having (meth)acryloyl group represented by the general formula (III) and the crosslinkable vinyl monomer, is dissolved in an mount of 100 ml of the good solvent at 25° C.

Concrete examples of the good solvent are, for instance, monohydric alcohols having 1 to 3 carbon atoms such as methanol, ethanol and isopropanol, acetone, ethyl acetate, benzene, toluene, xylene, and the like. Among those good solvents, ethanol, isopropanol and benzene are preferable since a copolymer having a relatively high molecular weight can be obtained. As the ethanol, ethanol having a purity of at least 95% by volume can be used, and it is desired that the ethanol has a purity of at least 99% by volume. When the obtained cationic thickener is used in cosmetics, since benzene and the like are harmful to human bodies, ethanol and isopropanol are more preferable.

In the present invention, a bad solvent can be mixed with the good solvent to precipitate a resulting copolymer from the reaction solution.

The bad solvent is intended to refer to a solvent in which a copolymer having a molecular weight of at least 10.000, which is prepared by copolymerizing the (meth)acrylic monomer having an amino group represented by the general formula (I) and the vinyl monomer represented by the general formula (II), is dissolved in an amount of at most 5 g per 100 ml of the bad solvent at 25° C.

Concrete examples of the bad solvent are, for instance, linear, branched or cyclic aliphatic hydrocarbons having at most 15 carbon atoms such as n-pentane, n-hexane and cyclohexane, and the like. Among those bad solvents, linear, branched or cyclic aliphatic hydrocarbons having at most 7 carbon atoms and a relatively high boiling point are preferable. Among them, linear, branched or cyclic aliphatic hydrocarbons having 6 or 7 carbon atoms are particularly preferable since those hydrocarbons have a high boiling point. Also, n-hexane, cyclohexane and the like are preferable because those hydrocarbons are cheap and industrially excellent in handling.

As a combination of the good solvent and the bad solvent, from the viewpoint that the polymerization degree of an obtained copolymer can be desirably adjusted before precipitating the copolymer, a combination of a monohydric alcohol having 1 to 3 carbon atoms and a linear, branched or cyclic hydrocarbon having at most 15 carbon atoms is preferable, and in particular, a combination of ethanol and cyclohexane is most preferable.

It is preferable that the good solvent and the bad solvent are admixed together in a suitable ratio so that the characteristics of an obtained cationic thickener are not lowered.

When the ratio of the bad solvent is too high, there is a tendency that the polymerization rapidly proceeds, powder is precipitated in a short period of time, and it becomes difficult to obtain a cationic thickener having desired physical properties. Therefore, it is desired that the content of the bad solvent in the mixture of the good solvent and the bad solvent is at most 98% by weight, preferably at most 97% by weight. Also, it is desired that the content of the bad solvent in the mixture of the good solvent and the bad solvent is at least 80% by weight, preferably at least 90% by weight in order to proceed the polymerization rapidly and aviod the aggregation and coagulation of a resulting copolymer during the removal of a solvent from the reaction solution.

It is necessary that a reactor is used for sufficiently stirring the monomer composition during the polymerization to efficiently give a cationic thickener from the reaction solution. When a general stirrer for solution polymerization is used, it is preferable that the concentration of the monomer composition is at most 30% by weight. Also, it is preferable that the monomer composition is sufficiently stirred with a stirrer or the like during the reaction in order to avoid the stagnation of reaction solution.

It is preferable that the polymerization reaction is carried out with heating to a temperature of 50° to 100° C. The polymerization reaction is generally carried out at a reflux temperature of a volatile-type solvent which is used in the reaction.

The preferable period of time necessary for the polymerization reaction is usually at least 10 hours. The polymerization reaction can be voluntarily terminated when the mount of the remaining monomer becomes at most 10% by weight.

The amount of the remaining moonomer can be determined by adding bromine to double bonds of the remaining monomer in accordance with a known method such as a PSDB method and measuring the amount of the double bonds.

Thus, a reaction solution containing the copolymer is obtained.

When the good solvent is used alone, a cationic thickener can be obtained in powder by removing the good solvent from the reaction solution.

Also, when a mixture of the good solvent and the bad solvent is used, a cationic thickener can be obtained in powder by filtrating a precipitated copolymer and then vacuum drying, or drying at atmospheric pressure or under reduced pressure.

During the polymerization reaction, a polymerization catalyst can be used. Examples of the polymerization catalyst are, for instance, 2,2'-azobisisobutyronitrile, 2,2'-azobis(4-methoxy-2,4-dimethylvaleronitrile), dimethyl-2,2'-azobisisobutylate, 2,2'-azobis(2,4-dimethylvaleronitrile), and the like. The kind of the polymerization catalyst is dependent on the boiling point of the used solvent. For instance, when ethanol or benzene is used as the solvent, 2,2'-azobisisobutyronitrile is most prefereble from the viewpoint of the easiness of handling. It is desired that the amount of the polymerization catalyst is 0.05 to 3% by weight, preferably 0.1 to 1% by weight based upon the weight of the whole mount of the monomer composition.

During the polymerization of the monomer, various appearances are exhibited.

When the good solvent is used solely, the same appearance as that shown in the conventional solution polymerization is exhibited in the early stages of the polymerization reaction. However, in the progress of the polymerization reaction, crosslinking reaction proceeds and a gelatinous appearance is shown. When the polymerization reaction further proceeds, a grease-like product having no precipitate is obtained.

When the mixture of the good solvent and the bad solvent is used, the same appearances as that shown in the conventional solution polymerization is exhibited in the early stages of the polymerization. However, in the progress of the polymerization reaction, the crosslinking reaction proceeds and the gelatinous appearance is shown. When the polymerization reaction further proceeds, the obtained polymer can be no longer dissolved in the mixed solvent, and is extracted from the reaction solution in the form of precipitate.

Thus, a cationic thickener is obtained. The cationic thickener usually has a viscosity of 3,000 to 90,000 cP, preferably 5,000 to 70,000 cP at 25° C. when the viscosity is measured by using a BH-type Brookfield viscometer commercially available from Tokyo Keiki Co., Ltd. (rotor No. 4) at 4 rpm after the cationic thickener is dispersed into water so that the concentration of the cationic thickener becomes 2% by weight, and the pH of the resulting aqueous cationic thickener is adjusted to 3.5 to 7 with lactic acid. Usually, after adjusting the pH value, the resulting aqueous cationic thickener is sufficiently stirred to obtain a clear and uniform aqueous cationic thickener.

When the cationic thickener is used as, for instance, a gel, the content of the cationic thickener is usually preferably adjusted to at most 3.5% by weight and the viscosity of the gel is adjusted to have a desired viscosity.

When a gel is prepared by using the cationic thickener, it is desired that the cationic thickener is diluted with water to a concentration of at most 2% by weight and neutralized with a mineral acid such as sulfuric acid, hydrochloric acid or phosphoric acid or an organic acid such as acetic acid, citric acid, lactic acid, amino acid, succinic acid, malic acid, dimethyl sulfate or diethyl sulfate.

The cationic thickener and the process for preparing the same of the present invention is more specifically described and explained by means of the following Examples. It is to be understood that the present invention is not limited to the Examples.

EXAMPLE 1

To a three-necked flask equipped with a thermometer, a reflux condenser and a tube for introducing nitrogen gas, 39 g of N,N-dimethylaminoethyl methacrylate, 58.5 g of N-vinylpyrrolidone, 2.5 g of methoxypolyethyleneglycol (23) methacrylate and 2 g of ethyleneglycol dimethacrylate, and a mixture of 33.4 g of ethanol and 464.6 g of cyclohexane (the weight ratio of the ethanol/cyclohexane: 6.7/93.3) were added so as to adjust the monomer content to 17% by weight. Then, the obtained mixture was stirred with refluxing at 80° C. for 2 hours in a stream of nitrogen gas to degas.

Then, 0.3 g of 2,2'-azobisisobutyronitrile was added to the three-necked flask to initiate the polymerization at 80° C.

The polymerization reaction was carried out for about 10 hours with stirring in a stream of nitrogen gas. Then, the obtained polymer slurry solution was filtrated under reduced pressure and the obtained solid was dried under reduced pressure.

The obtained dried polymer was pulverized to obtain a white powdered cationic thickener.

Then, water was added to the cationic thickener so that the concentration of the cationic thickener became 2% by weight, and its pH was adjusted to 6.4 by using lactic acid as a neutralizer. The mixture was stirred thoroughly by using a homogenizer to obtain a gel.

As the physical properties of the obtained gel, viscosity, feel, appearance, flexibility of a formed film and gloss of a formed film were investigated. The results are shown in Table 1.

(A) Viscosity

The viscosity was measured at a temperature of 25° C., using a BH-type (Rotor No. 4, rotation: 4 rpm) Brookfield viscometer commercially available from Tokyo Keiki Co., Ltd.

(B) Feel

The feel was examined by holding about 2 ml of the obtained gel between fingers and rubbing the gel. The feel was evaluated in accordance with the following criteria for evaluation.

[Criteria for evaluation]
A: Smooth and light feeling
B: A little rough feeling
C: Somewhat rough feeling
D: Remarkably rough feeling (C) Appearance Whether the obtained gel was contaminated with impurities or not was examined by observing the obtained gel with naked eyes. The appearance was evaluated in accordance with the following criteria for evaluation.

[Criteria for evaluation]
A: No contamination of impurities was observed.
B: A little contamination of impurities was observed.
C: Contamination of impurities was somewhat observed.
D: Contamination of impurities was remarkably observed.

(D) Flexibility of a formed film

The obtained gel was coated on a film made of a vinyl chloride resin by using a bar coater so that a film of the gel having a thickness of 10 μm could be obtained. A film was formed by air drying for 3 hours, and the film made of the vinyl chloride resin was randomly bent. The state of the formed film of the gel was observed with naked eyes. Then, the flexiblity was evaluated in accordance with the following criteria for evaluation.

[Criteria for evaluation]
A: No change was observed.
B: Peeling was slightly observed.
C: Peeling was observed in part.
D: Perfect peeling was observed.

(E) Gloss of a formed film

The film which was formed in the above-mentioned item (D) was observed with naked eyes. The gloss was evaluated in accordance with the following criteria for evaluation.

[Criteria for evaluation]
A: The film had a gloss.
B: The film had a little gloss.
C: The film had no gloss.

EXAMPLES 2 to 17

White powdered cationic thickeners were obtained in the same manner as in Example 1 except that monomers having (meth)acryloyl group as shown in Table 1 were used instead of methoxypolyethyleneglycol(23) methacrylate.

Then, gels were prepared by using the obtained cationic thickener in the same manner as in Example 1, and the physical properties thereof were examined. The results are shown in Table 1.

COMPARATIVE EXAMPLE 1

To a three-necked flask equipped with a thermometer, a reflux condenser and a tube for introducing nitrogen gas, 39 g of N,N-dimethylaminoethyl methacrylate, 61 g of N-vinylpyrrolidone and 2 g of ethyleneglycol dimethacrylate were added, and the concentration of the monomers was adjusted to 17% by weight by adding a mixture of 33.4 g of ethanol and 464.6 g of cyclohexane thereto. Then, the obtained mixture was stirred for 2 hours in a stream of nitrogen gas with refluxing at 80° C. to degas the mixture.

Then, 0.3 g of 2,2'-azobisisobutyronitrile was added to the flask, and the polymerization reaction was carried out at 80° C. for about 10 hours with stirring in a stream of nitrogen gas. After that, the obtained polymer slurry solution was filtrated under reduced pressure, and the obtained solid was dried under reduced pressure.

The dried polymer was pulverized to obtain a white powdered cationic thickener. A gel was prepared by using the obtained cationic thickener in the same manner as in Example 1 and then the physical properties thereof were examined. The results are also shown in Table 1.

EXAMPLE 18

To a four-necked flask equipped with a mechanical stirrer, a thermometer, a reflux condenser and a tube for introducing nitrogen gas, 50 g of N,N-dimethylaminoethyl methacrylate, 47.5 g of N-vinylpyrrolidone, 2.5 g of stearyl acrylate and 1.9 g of tripropylene glycol diacrylate, and a mixture of 23.1 g of ethanol and 554.3 g of cyclohexane (the weight ratio of the ethanol/cyclohexane: 4/96) were added. Then, the obtained mixture was stirred with refluxing at 80° C. for 2 hours in a stream of nitrogen gas to degas.

Then, 0.41 g of 2,2'-azobisisobutyronitrile was added to the four-necked flask to initiate the polymerization at 80° C. After 45 minutes passed from the initiation of the polymerization, 1.9 g of tripropylene-glycol diacrylate was added thereto. After further 45 minutes passed, 1.9 g of tripropyleneglycol diacrylate was added thereto. The polymerization reaction was carried out for about 10 hours with stirring in a stream of nitrogen gas. Then, the obtained polymer slurry solution was filtrated under reduced pressure and the obtained solid was dried under reduced pressure.

The obtained dried polymer was pulverized with a pulverizer to obtain a white powdered cationic thickener.

Then, distilled water was added to the cationic thickener so that the concentration of the cationic thickener became 2% by weight, and its pH was adjusted by using lactic acid as a neutralizer. The mixture was stirred for about 5 hours by using a stirrer equipped with a propeller blade to obtain a transparent gel.

The physical properties of the obtained gel were examined in the same manner as in Example 1. The results are shown in Table 2.

EXAMPLES 19 to 21

White powdered cationic thickeners were obtained in the same manner as in Example 18 except that monomers containing (meth)acryloyl group as shown in Table 2 were used instead of stearyl acrylate.

Then, gels were prepared by using the obtained cationic thickener in the same manner as in Example 18, and the physical properties thereof were examined. The results are shown in Table 2.

EXAMPLE 22

A white powdered cationic thickener was obtained in the same manner as in Example 18 except that N,N-dimethylaminopropylmethacrylamide was used instead of N,N-dimethylaminoethyl methacrylate.

Then, a gel was prepared by using the obtained cationic thickener in the same manner as in Example 18, and the physical properties thereof were examined. The results are shown in Table 2.

EXAMPLE 23

To a four-necked flask equipped with a mechanical stirrer, a thermometer, a reflux condenser and a tube for introducing nitrogen gas, 50 g of N,N-dimethylaminoethyl methacrylate, 47.5 g of methacrylamide, 2.5 g of stearyl acrylate and 1.9 g of tripropyleneglycol diacrylate were added as monomers, and the concentration of the monomers was adjusted so as to become 21% by weight by adding 376.2 g of ethanol thereto. Then, the obtained mixture was stirred for 2 hours in a stream of nitrogen gas with refluxing at 80° C. to degas the mixture.

Then, 0.41 g of 2,2'-azobisisobutyronitrile was added to the four-necked flask, and the polymerization was initiated at 80° C. After 45 minutes passed from the initiation of the polymerization, 1.9 g of tripropylene-glycol diacrylate was added to the four-necked flask, and after further 45 minutes passed, 1.9 g of tripropylene-glycol diacrylate was added to the four-necked flask. The polymerization reaction was carried out for about 10 hours with stirring in a stream of nitrogen gas. After that, the obtained polymer slurry solution was filtrated under reduced pressure, and the obtained solid was dried under reduced pressure.

The dried polymer was pulverized by using a pulverizer to obtain a white powdered cationic thickener. A gel was prepared using the obtained cationic thickener in the same manner as in Example 18 and then the physical properties thereof were examined. The results are also shown in Table 2.

Then, gels were prepared using the obtained cationic thickeners in the same manner as in Example 18, and the physical properties thereof were examined. The results are also shown in Table 2.

EXAMPLES 28 and 29

White powederd cationic thickeners were obtained using raw materials shown in Table 2 in the same manner as in Example 18 except that the amount of tripropyleneglycol diacrylate was divided into three, and the divided tripropyleneglycol diacrylate was added to the four-necked flask in the same manner as in Example 18.

Then, gels were prepared using the obtained cationic thickeners in the same manner as in Example 18, and the physical properties thereof were examined. The results are shown in Table 2.

EXAMPLES 30 to 34

White powdered cationic thickeners were obtained using raw materials shown in Table 2 in the same manner as in Example 18.

Then, gels were prepared using the obtained cationic thickeners in the same manner as in Example 18, and the physical properties thereof were examined. The results are also shown in Table 2.

TABLE 1

| | Monomer having (meth)acryloyl group | Physical properties of gel | | | | |
|---|---|---|---|---|---|---|
| | | Viscosity (cP) | Feel | Appearance | Flexibility of formed film | Gloss of formed film |
| Example No. 1 | Methoxypolyethyleneglycol(23) methacrylate | 41000 | A | A | A | A |
| 2 | Polyethyleneglycol (2) monomethacrylate | 49000 | A | A | A | A |
| 3 | Methoxypolyethyleneglycol (4) methacrylate | 40000 | A | A | A | A |
| 4 | Methoxypolyethyleneglycol (2) methacrylate | 39000 | A | A | A | A |
| 5 | Polyethyleneglycol (7 to 9) monomethacrylate | 50000 | A | A | A | A |
| 6 | Methoxypolyethyleneglycol (9) methacrylate | 40000 | A | A | A | A |
| 7 | Methyl methacrylate | 32000 | A | A | A | B |
| 8 | n-Butyl methacrylate | 40000 | A | A | A | A |
| 9 | t-Butyl methacrylate | 39000 | A | A | A | A |
| 10 | Hexyl methacrylate | 39500 | A | A | A | A |
| 11 | Isodecyl methacrylate | 41200 | A | A | A | A |
| 12 | Lauryl methacrylate | 40300 | A | A | A | A |
| 13 | Stearyl methacrylate | 40500 | A | A | A | A |
| 14 | 2-Hydroxyethyl methacrylate | 32000 | A | A | A | B |
| 15 | Polypropyleneglycol (7 to 9) monomethacrylate | 41000 | A | A | A | A |
| 16 | N-t-octyl methacrylamide | 39800 | A | A | A | A |
| 17 | N-t-octyl acrylamide | 38300 | A | A | A | A |
| Comparative Example 1 | — | 27000 | A | A | B | C |

EXAMPLES 24 to 27

White powdered cationic thickeners were obtained using raw materials shown in Table 2 in the same manner as in Example 18.

TABLE 2

| Example No. | Components of monomer composition for a thickener (g) | | | | | |
|---|---|---|---|---|---|---|
| | (Meth)acrylic monomer having an amino group | Vinyl monomer | Monomer having (meth)acryloyl group | Crosslinkable vinyl monomer | Solvent (g) Good solvent | Bad solvent |
| 18 | NDAEMA (50) | NVP (47.5) | STA (2.5) | TPGDA (5.7) | ET (23.1) | CH (554.3) |
| 19 | NDAEMA (50) | NVP (47.5) | LMA (2.5) | TPGDA (5.7) | ET (23.1) | CH (554.3) |
| 20 | NDAEMA (50) | NVP (47.5) | NOAA (2.5) | TPGDA (5.7) | ET (23.1) | CH (554.3) |
| 21 | NDAEMA (50) | NVP (47.5) | MPEGMA (2.5) | TPGDA (5.7) | ET (23.1) | CH (554.3) |
| 22 | NDAPMA (50) | NVP (47.5) | STA (2.5) | TPGDA (5.7) | ET (23.1) | CH (554.3) |
| 23 | NDAEMA (50) | MAA (47.5) | STA (2.5) | TPGDA (5.7) | ET (376.2) | — |
| 24 | NDAEMA (21.1) | NVP (76.3) | STA (2.5) | TPGDA (5.7) | ET (23.1) | CH (554.3) |
| 25 | NDAEMA (84.6) | NVP (12.9) | STA (2.5) | TPGDA (5.7) | ET (23.1) | CH (554.3) |
| 26 | NDAEMA (35.4) | NVP (32.9) | STA (31.7) | TPGDA (5.7) | ET (23.1) | CH (554.3) |
| 27 | NDAEMA (35.4) | NVP (6.5) | STA (58.1) | TPGDA (5.7) | ET (23.1) | CH (554.3) |
| 28 | NDAEMA (50) | NVP (42.6) | STA (2.5) | TPGDA (10.5) | ET (23.1) | CH (554.3) |
| 29 | NDAEMA (50) | NVP (37.3) | STA (2.5) | TPGDA (15.9) | ET (23.1) | CH (554.3) |
| 30 | NDAEMA (50) | NVP (47.5) | LA (2.5) | TPGDA (5.7) | ET (23.1) | CH (554.3) |
| 31 | NDAEMA (50) | NVP (47.5) | BA (2.5) | TPGDA (5.7) | ET (23.1) | CH (554.3) |
| 32 | NDAEMA (50) | NVP (47.5) | STA (2.5) | TPGDA (7.5) | ET (21.3) | CH (587.8) |
| 33 | NDAEMA (50) | NVP (47.5) | STA (2.5) | TPGDA (7.5) | ET (21.3) | CH (587.8) |
| 34 | NDAEMA (50) | NVP (47.5) | STA (2.5) | TPGDA (7.5) | ET (43.0) | CH (387.0) |

| Example No. | Concentration of monomer composition for a thickener (% by weight) | Polymerization catalyst (g) | Physical properties of gel | | | | |
|---|---|---|---|---|---|---|---|
| | | | Viscosity (cP) | Feel | Appearance | Flexibility of formed film | Gloss of formed film |
| 18 | 15 | AIBN (0.41) | 13800 | A | A | A | A |
| 19 | 15 | AIBN (0.41) | 15000 | A | A | A | A |
| 20 | 15 | AIBN (0.41) | 16200 | A | A | A | A |
| 21 | 15 | AIBN (0.41) | 12000 | A | A | A | A |
| 22 | 15 | AIBN (0.41) | 12000 | A | A | A | A |
| 23 | 22 | AIBN (0.41) | 9000 | A | A | A | A |
| 24 | 15 | AIBN (0.41) | 6600 | A | A | A | A |
| 25 | 15 | AIBN (0.41) | 24000 | A | A | A | A |
| 26 | 15 | AIBN (0.41) | 12600 | A | A | A | A |
| 27 | 15 | AIBN (0.41) | 13800 | A | A | A | A |
| 28 | 15 | AIBN (0.41) | 18600 | A | A | A | A |
| 29 | 15 | AIBN (0.41) | 23400 | A | A | A | A |
| 30 | 15 | AIBN (0.41) | 15600 | A | A | A | A |
| 31 | 15 | AIBN (0.41) | 13800 | B | A | B | B |
| 32 | 15 | DAMP | 41400 | A | A | A | A |

TABLE 2-continued

| | | (0.38) | | | | | |
|---|---|---|---|---|---|---|---|
| 33 | 15 | TBPO | 66000 | A | A | A | A |
| | | (0.64) | | | | | |
| 34 | 20 | AIBN | 103200 | B | A | A | A |
| | | (0.32) | | | | | |

In Table 2, each abbreviation is intended to refer to the following compounds.
NDAEMA: N,N-dimethylaminoethyl methacrylate
NDAPMA: N,N-dimethylaminopropylmethacrylamide
NVP: N-vinylpyrrolidone
MAA: methacrylamide
STA: stearyl acrylate
LMA: lauryl methacrylate
NOAA: N-t-octylacrylamide
MPEGMA: methoxypolyethylene glycol (23) methacrylate
TPGDA: tripropyleneglycol diacrylate
ET: ethanol
CH: cyclohexane
AIBN: 2,2'-azobisisobutyronitrile
LA: Lauryl acrylate
BA: n-Butyl acrylate
DAMP: Dimethyl 2,2'-azobis(2-methylpropionate)
TBPO: t-Butylperoxy 2-ethylhexanoate

EXAMPLE 35

To a three-necked flask equipped with a thermometer, a reflux condenser and a tube for introducing nitrogen gas, 39 g of N,N-dimethylaminoethyl methacrylate, 55.9 g of N-vinylpyrrolidone, 5.1 g of methoxypolyethyleneglycol(23) methacrylate and 2 g of ethyleneglycol dimethacrylate were added, and the concentration of the monomers was adjusted to 17% by weight by adding a mixture of 33.4 g of ethanol and 464.6 g of cyclohexane thereto. Then, the obtained mixture was stirred for 2 hours in a stream of nitrogen gas with refluxing at 80° C. to degas the mixture.

Then, 0.3 g of 2,2'-azobisisobutyronitrile was added to the flask, and the polymerization reaction was carried out at 80° C. for about 10 hours with stirring in a stream of nitrogen gas. After that, the obtained polymer slurry solution was filtrated under reduced pressure, and the obtained solid was dried under reduced pressure.

The dried polymer was pulverized to obtain a white powdered cationic thickener. A gel was prepared by using the obtained cationic thickener in the same manner as in Example 1 and then the physical properties thereof were examined. The results are shown in Table 3.

EXAMPLE 36

A white powdered cationic thickener was obtained in the same manner as in Example 35 except that the amount of N-vinylpyrrolidone was changed to 46 g and the amount of methoxypolyethyleneglycol(23) methacrylate was changed to 15 g.

Then, gels were prepared by using the obtained cationic thickener in the same manner as in Example 35, and then the physical properties thereof were examined. The results are also shown in Table 3.

EXAMPLE 37

To a three-necked flask equipped with a thermometer, a reflux condenser and a tube for introducing nitrogen gas, 46 g of N,N-dimethylaminoethyl methacrylate, 4 g of N-vinylpyrrolidone, 50 g of methoxypolyethyleneglycol(23) methacrylate and 3.5 g of ethyleneglycol dimethacrylate were added, and the concentration of the monomers was adjusted to 21% by weight by adding 389.4 g of ethanol thereto. Then, the obtained mixture was stirred for 2 hours in a stream of nitrogen gas with refluxing at 80° C. to degas the mixture.

Then, 0.3 g of 2,2'-azobisisobutyronitrile was added to the flask, and the polymerization reaction was carried out at 80° C. for about 10 hours with stirring in a stream of nitrogen gas. After that, the obtained transparent and greasy polymer was dried on a stainless-steel vat under reduced pressure.

The dried polymer was pulverized to obtain a pale yellow powdered cationic thickener. A gel was prepared by using the obtained cationic thickener in the same manner as in Example 35 and then the physical properties thereof were examined. The results are also shown in Table 3.

COMPARATIVE EXAMPLE 2

To a three-necked flask equipped with a thermometer, a reflux condenser and a tube for introducing nitrogen gas, 30 g of N,N-dimethylaminoethyl methacrylate, 5 g of N-vinylpyrrolidone, 65 g of methoxypolyethyleneglycol(23) methacrylate and 3.5 g of ethyleneglycol dimethacrylate were added, and the concentration of the monomers was adjusted to 21% by weight by adding 389.4 g of ethanol thereto. Then, the obtained mixture was stirred for 2 hours in a stream of nitrogen gas with refluxing at 80° C. to degas the mixture.

Then, 0.3 g of 2,2'-azobisisobutyronitrile was added to the flask, and the polymerization reaction was carried out at 80° C. for about 10 hours with stirring in a stream of nitrogen gas. After that, the obtained transparent and greasy polymer was dried on a stainless-steel vat under reduced pressure.

The dried polymer was pulverized to obtain a pale yellow powdered cationic thickener. A gel was prepared by using the obtained cationic thickener in the same manner as in Example 1, and then the physical properties thereof were examined. The results are also shown in Table 3.

TABLE 3

| | Physical properties of gel | | | | |
|---|---|---|---|---|---|
| Example No. | Viscosity (cP) | Feel | Appearance | Flexibility of formed film | Gloss of formed film |
| 35 | 48500 | A | A | A | A |
| 36 | 50000 | A | A | A | A |
| 37 | 30600 | A | B | A | A |
| Comparative Example 2 | 18550 | C | C | A | C |

EXAMPLES 38 to 40

White powdered cationic thickeners were obtained in the same manner as in Example 1 except that 39 g of a (meth)acrylic monomer having an amino group shown in Table 4 was used instead of N,N-dimethylaminoethyl methacrylate.

Then, gels were prepared by using the obtained cationic thickeners in the same manner as in Example 1, and the physical properties thereof were examined. The results are shown in Table 4.

acrylamide, 2.5 g of methoxypolyethyleneglycol(23) methacrylate and 3.0 g of ethyleneglycol dimethacrylate were added, and the concentration of the monomers was adjusted to 21% by weight by adding 387.5 g of ethanol thereto. Then, the obtained mixture was stirred for 2 hours in a stream of nitrogen gas with refluxing at 80° C. to degas the mixture.

Then, 0.3 g of 2,2'-azobisisobutyronitrile was added to the flask, and the polymerization reaction was carried out at 80° C. for about 10 hours with stirring in a stream of nitrogen gas. After that, the obtained polymer slurry solution was

TABLE 4

| Example No. | (Meth)acrylic monomer having an amino group | Physical properties of gel | | | | |
|---|---|---|---|---|---|---|
| | | Viscosity (cP) | Feel | Appearance | Flexibility of formed film | Gloss of formed film |
| 38 | N,N-dimethylaminoethyl acrylate | 39500 | A | A | A | A |
| 39 | N,N-dimethylaminopropyl methacrylamide | 33000 | A | A | A | A |
| 40 | N,N-dimethylaminopropyl acrylamide | 30500 | A | A | A | A |

EXAMPLE 41

To a three-necked flask equipped with a thermometer, a reflux condenser and a tube for introducing nitrogen gas, 80 g of N,N-dimethylaminoethyl methacrylate, 20 g of methoxypolyethyleneglycol(23) methacrylate and 3 g of ethyleneglycol dimethacrylate were added, and the concentration of the monomers was adjusted to 17% by weight by adding a mixture of 33.7 g of ethanol and 469.2 g of cyclohexane thereto. Then, the obtained mixture was stirred for 2 hours in a stream of nitrogen gas with refluxing at 80° C. to degas the mixture.

Then, 0.3 g of 2,2'-azobisisobutyronitrile was added to the flask, and the polymerization reaction was carried out at 80° C. for about 10 hours with stirring in a stream of nitrogen gas. After that, the obtained transparent and greasy polymer was dried on a stainless-steel vat under reduced pressure.

The dried polymer was pulverized to obtain a pale yellow powdered cationic thickener. A gel was prepared by using the obtained cationic thickener in the same manner as in Example 1, and then the physical properties thereof were examined. The results are shown in Table 5.

EXAMPLE 42

To a three-necked flask equipped with a thermometer, a reflux condenser and a tube for introducing nitrogen gas, 45 g of N,N-dimethylaminoethyl methacrylate, 52.5 g of meth-filtrated under reduced pressure, and the obtained solid was dried under reduced pressure.

The dried polymer was pulverized to obtain a white powdered cationic thickener. A gel was prepared by using the obtained cationic thickener in the same manner as in Example 1, and then the physical properties thereof were examined. The results are also shown in Table 5.

TABLE 5

| | Physical properties of gel | | | | |
|---|---|---|---|---|---|
| Example No. | Viscosity (cP) | Feel | Appearance | Flexibility of formed film | Gloss of formed film |
| 41 | 29700 | A | A | A | A |
| 42 | 30300 | A | A | A | A |

EXAMPLES 43 to 60 and COMPARATIVE EXAMPLES 3 to 8

The cationic thickener which was obtained in Example 1, Example 13, Example 16 or Comparative Example 1 was mixed with water and ethanol in an amount shown in Table 6, and then its pH was adjusted to 6.5 by using lactic acid.

As a setting polymer, a nonionic polymer for setting (N-vinylpyrrolidone-vinyl acetate copolymer commercially available from Osaka Yuki Kagaku Kogyo Kabushiki Kaisha under the trade name of PVA-6450), a cationic polymer for setting (diethyl sulfate of N-vinylpyrrolidone-N, N-dimethylaminoethyl methacrylate copolymer commercially available from Osaka Yuki Kagaku Kogyo Kabushiki Kaisha under the trade name of HCP-3A) or an amphoteric polymer for setting (N-methacryloylethyl-N, N-dimethylammonium-α-N-methylcarboxybetaine-methacrylic acid ester copolymer commercially available from Mitsubishi Petrochemical Co., Ltd., under the trade name of Yukaformer AM75) was gradually added thereto in a amount shown in Table 6. The mixture was stirred by using a stirrer equipped with a propeller blade until the mixture became uniform to give a setting gel for hair.

As the physical properties of the obtained setting gel, viscosity, transparency, setting property, feel, flaking and facility for shampooing were examined in accordance with the following methods. The results are shown in Table 6.

(A) Viscosity

The viscosity was measured at a temperature of 25° C. by using a BH-type Brookfield viscometer commercially available from Tokyo Keiki Co., Ltd. (rotor No. 4) at 4 rpm.

(B) Transparency

An amount of 30 g of the obtained setting gel was weighed and a glass cell for measuring turbidity was charged with the setting gel. After the gel was defoamed at room temperature for 1 hour by using an ultrasonic cleaner, the glass cell was set in a 18900-00 type Ratio turbidimeter commercially available from HACH COMPANY and allowed to stand for 15 minutes for stabilizing the measured value. Then, the value of turbidity was read off and the transparency was evaluated in accordance with the following criteria for evaluation.

[Criteria for evaluation]
A: Less than 3 NTU
B: At least 3 NTU and less than 5 NTU
C: At least 5 NTU (C) Setting property An amount of 3 g of the obtained setting gel was uniformly applied to 2 g of hair having a length of 25 cm with hand. This hair was wound around a curler having an outside diameter of 1.2 cm, and the hair was dried by hot air of 40° C. for 60 minutes. Then, the hair was removed from the curler and the hair was perpendicularly hung in an atmosphere having a relative humidity of 80% and a temperature of 30° C. The length just after hanging (L1) and the length after hanging for 1 hour (L2) were measured and the curl retention value was calculated in accordance with the equation:

$$(\text{Curl retention value}) = \frac{25 - L2 \text{ (cm)}}{25 - L1 \text{ (cm)}} \times 100 \text{ (\%)}$$

The greater the curl retention value is, the better the setting property is. In the present invention, when the curl retention value is at least 60%, the setting gel can be satisfactorily used.

(D) Feel

The feel was examined by holding about 2 ml of the obtained setting gel between fingers and rubbing the setting gel. The feel was evaluated in accordance with the following criteria for evaluation.

[Criteria for evaluation]

A: Smooth and light feeling.
B: Little rough feeling.
C: Somewhat rough feeling.
D: Remarkably rough feeling.

(E) Flaking

An amount of 3 g of the setting gel was uniformly applied to hair having a length of 25 cm, and the excessive gel was removed by stroking with hand.

This hair was dried by hot air of 40° C. for 60 minutes to form a film on the surface of the hair, and the hair was combed 10 times by using a comb. Then, the film was evaluated in accordance with the following criteria for evaluation.

[Criteria for evaluation]

A: No peeling was observed.
B: Peeling was observed in part.
C: Peeling was observed throughout.

(F) Facility for shampooing

An amount of 3 g of the setting gel was uniformly applied to 2 g of hair having a length of 25 cm. After the hair was dried by hot air of 40° C. for 60 minutes, the hair was soaked in warm water containing 0.5% of a marketed shampoo having a temperature of 30° C., and the warm water was stirred. The condition of the removal of the setting gel was observed, and the facility for shampooing was evaluated in accordance with the following criteria for evaluation.

[Criteria for evaluation]

A: Within 30 minutes, the setting gel could be completely removed by washing without slime.
B: Within 40 minutes, the setting gel could be completely removed by washing without slime.
C: After 40 minutes passed, the setting gel somewhat remained and a little slime was observed.
D: The setting gel could not be removed by washing and slime remained after 40 minutes passed.

The mark "*" described in Table 6 is intended to mean that a gel was not generated.

TABLE 6

| | Components of setting gel (g) | | | | Physical properties of setting gel | | | | | |
|---|---|---|---|---|---|---|---|---|---|---|
| | Cationic thickener | Distilled water | Ethanol | Polymer for setting | Viscosity (cP) | Transparency | Setting property (%) | Feel | Flaking | Facility for shampooing |
| Example No. | | | | | | | | | | |
| 43 | Cationic thickener obtained in Example 1 (1.72) | (74.28) | (10) | Nonionic polymer for setting (14) | 37000 | A | 73 | A | A | A |
| 44 | Cationic thickener | (74.28) | (10) | Nonionic | 39000 | A | 75 | A | A | A |

TABLE 6-continued

| | Components of setting gel (g) | | | | Physical properties of setting gel | | | | | |
|---|---|---|---|---|---|---|---|---|---|---|
| | Cationic thickener | Distilled water | Ethanol | Polymer for setting | Viscosity (cP) | Transparency | Setting property (%) | Feel | Flaking | Facility for shampooing |
| 45 | obtained in Example 13 (1.72) Cationic thickener obtained in Example 16 (1.72) | (74.28) | (10) | polymer for setting (14) Nonionic polymer for setting (14) | 32500 | A | 76 | A | A | A |
| 46 | Cationic thickener obtained in Example 1 (1.6) | (68.4) | (10) | Nonionic polymer for setting (20) | 29000 | A | 89 | A | A | A |
| 47 | Cationic thickener obtained in Example 13 (1.6) | (68.4) | (10) | Nonionic polymer for setting (20) | 35000 | A | 90 | A | A | A |
| 48 | Cationic thickener obtained in Example 16 (1.6) | (68.4) | (10) | Nonionic polymer for setting (20) | 26000 | A | 89 | A | A | B |
| 49 | Cationic thickener obtained in Example 1 (1.72) | (74.28) | (10) | Cationic polymer for setting (14) | 35000 | A | 73 | A | A | A |
| 50 | Cationic thickener obtained in Example 13 (1.72) | (74.28) | (10) | Cationic polymer for setting (14) | 36000 | A | 74 | A | A | A |
| 51 | Cationic thickener obtained in Example 16 (1.72) | (74.28) | (10) | Cationic polymer for setting (14) | 30000 | A | 73 | A | A | A |
| 52 | Cationic thickener obtained in Example 1 (1.6) | (68.4) | (10) | Cationic polymer for setting (20) | 25000 | A | 85 | A | A | A |
| 53 | Cationic thickener obtained in Example 13 (1.6) | (68.4) | (10) | Cationic polymer for setting (20) | 25000 | A | 86 | A | A | A |
| 54 | Cationic thickener obtained in Example 16 (1.6) | (68.4) | (10) | Cationic polymer for setting (20) | 20500 | A | 85 | A | A | A |
| 55 | Cationic thickener obtained in Example 1 (1.72) | (74.28) | (10) | Amphoteric polymer for setting (14) | 38000 | A | 75 | A | A | A |
| 56 | Cationic thickener obtained in Example 13 (1.72) | (74.28) | (10) | Amphoteric polymer for setting (14) | 39000 | A | 77 | A | A | A |
| 57 | Cationic thickener obtained in Example 16 (1.72) | (74.28) | (10) | Amphoteric polymer for setting (14) | 33000 | A | 76 | A | A | A |
| 58 | Cationic thickener obtained in Example 1 (1.6) | (68.4) | (10) | Amphoteric polymer for setting (20) | 22000 | A | 87 | A | A | A |
| 59 | Cationic thickener obtained in Example 13 (1.6) | (68.4) | (10) | Amphoteric polymer for setting (20) | 32000 | A | 89 | A | A | A |
| 60 | Cationic thickener obtained in Example 16 (1.6) | (68.4) | (10) | Amphoteric polymer for setting (20) | 20000 | A | 88 | A | A | A |
| Comparative Example No. | | | | | | | | | | |
| 3 | Cationic thickener obtained in Comparative Example 1 (1.72) | (74.28) | (10) | Nonionic polymer for setting (14) | 19000 | A | 72 | A | A | A |
| 4 | Cationic thickener obtained in Comparative Example 1 | (68.4) | (10) | Nonionic polymer for setting (20) | * | A | 82 | A | B | B |
| 5 | Cationic thickener obtained in Comparative Example 1 (1.72) | (74.28) | (10) | Cationic polymer for setting (14) | 19000 | A | 72 | A | A | A |
| 6 | Cationic thickener obtained in Comparative Example 1 (1.6) | (68.4) | (10) | Cationic polymer for setting (20) | * | B | 83 | B | A | A |
| 7 | Cationic thickener obtained in Comparative Example 1 (1.72) | (74.28) | (10) | Amphoteric polymer for setting (14) | 16000 | A | 70 | A | A | A |
| 8 | Cationic thickener obtained in Comparative Example 1 (1.6) | (68.4) | (10) | Amphoteric polymer for setting (20) | * | C | 75 | B | A | A |

As is clear from the results shown in Table 6, gels for hair setting in which the cationic thickener of the present invention is used are excellent in physical properties such as facility for shampooing and setting property, and also show excellent gel-forming property nevertheless the amount of the cationic thickener is small.

Furthermore, the gels can be easily added to various resins for setting.

The cationic thickener of the present invention forms a film having excellent flexibility on hair and contains little impurities such as residue. When the cationic thickener is used in, for instance, an agent for hair setting, the cationic thickener imparts excellent setting properties to hair.

According to the process for preparing a cationic thickener of the present invention, a cationic thickener which forms a film having excellent flexibility can be easily obtained.

EXAMPLES 61 to 86

The cationic thickener which was obtained in Example 18, Example 20, Example 22, Example 23 or Example 31 was mixed with distilled water and ethanol in the amount shown in Table 7, and then its pH was adjusted to 6.5 by using lactic acid.

As a setting polymer, a nonionic polymer for setting (N-vinylpyrrolidone-vinyl acetate copolymer commercially available from Osaka Yuki Kagaku Kogyo Kabushiki Kaisha under the trade name of PVA-6450), a cationic polymer for setting (diethyl sulfate of N-vinylpyrrolidone-N,N-dimethylaminoethyl methacrylate copolymer commercially available from Osaka Yuki Kagaku Kogyo Kabushiki Kaisha under the trade name of HCP-3A) and an amphoteric polymer for setting (N-methacryloyl-ethyl-N, N-dimethylammonium-α-N-methylcarboxybetaine-methacrylic acid ester copolymer commercially available from Mitsubishi Petrochemical Co., Ltd., under the trade name of Yukaformer AM75) was gradually added thereto in the amount shown in Table 7. The mixture was stirred by using a stirrer equipped with a propeller blade until the mixture became uniform to give a setting gel for hair.

As the physical properties of the obtained setting gel, viscosity, transparency, setting property, feel, flaking and facility for shampooing were examined in the same manner as in Examples 43 to 60. The results are shown in Table 7.

COMPARATIVE EXAMPLE 9

To a three-necked flask equipped with a stirrer, a reflux condenser and a thermometer, 120 g of water and 0.5 g of Emulgen 950 commercially available from Kao Corporation as an emulsifier were added, and heated to 80° C. Then, to the flask, 0.15 g of sodium salt of 4,4'-azobis-(4-cyanovaleric acid) was added.

After that, an emulsion was previously prepared by mixing 185 g of a monomer mixture composed of 38.9% by weight of N,N-dimethylaminoethyl methacrylate, 58.4% by weight of N-vinylpyrrolidone, 2.6% by weight of n-butyl methacrylate and 0.1% by weight of ethyleneglycol dimethacrylate with 180 g of water, 14.5 g of Emulgen 950 commercially available from Kao Corporation as an emulsifier and 0.05 g of sodium salt of 4,4'-azobis-(4-cyanovaleric acid) as an initiator, and copolymerizing the moonomer mixture.

The resulting emulsion was added to the flask dropwise for about 2 hours, and its reaction was carried out at 80° C. for one hour to give a thickener.

The obtained thickener was dried and the resulting dried matter was conducted to the measurement of infrared ray spectrum. Also, one gram of the reaction was dissolved in 50 ml of ethyl alcohol and its acid value was measured with Thymol Blue.

During the reaction, the viscosity of the reaction solution increased and the mixing of the reaction solution was so difficult. This means that N,N-dimethylaminoethyl methacrylate itself or contained in the- resulting polymer was hydrolyzed and its viscosity increased. This hydrolysis was ascertained by measuring the infrared ray spectrum of the obtained thickener. That is, when the infrared ray spectrum was measured, an absorption band was observed around at 2500 $cm^{-1}$ based upon ammonium ion. This absorption shows that N,N-dimethylaminoethanol and a carboxylic acid salt were generated by the hydrolysis of N,N-dimethylaminoethyl methacrylate.

Also, when the acid value of the obtained thickener was measured, it was confirmed that 30% by weight of N,N-dimethylaminoethyl methacrylate was hydrolized.

The obtained thickener was mixed with water and ethanol in an amount shown in Table 7, and its pH was adjusted to 6.5 by using lactic acid.

As a setting polymer, the same nonionic polymer for setting as used in Example 61 was used and gradually added to the obtained thickener in an amount shown in Table 7. The mixture was stirred by using a stirrer equipped with a propeller blade until the mixture became uniform to give a setting gel for hair.

The physical properties of the obtained setting gel for hair were examined in the same manner as in Example 61. The results are shown in Table 7.

TABLE 7

| | Components of setting gel (g) | | | | Physical properties of setting gel | | | | | |
|---|---|---|---|---|---|---|---|---|---|---|
| | Cationic thickener | Distilled water | Ethanol | Polymer for setting | Viscosity (cP) | Transparency | Setting property (%) | Feel | Flaking | Facility for shampooing |
| Example No. | | | | | | | | | | |
| 61 | Cationic thickener obtained in Example 18 (3.5) | (66.5) | (10) | Nonionic polymer for setting (14) | 10500 | A | 75 | A | A | A |
| 62 | Cationic thickener obtained in Example 20 (3.5) | (66.5) | (10) | Nonionic polymer for setting (14) | 10300 | A | 75 | A | A | A |
| 63 | Cationic thickener obtained in Example 22 (3.5) | (66.5) | (10) | Nonionic polymer for setting (14) | 8600 | A | 80 | A | A | A |
| 64 | Cationic thickener | (66.5) | (10) | Nonionic | 7800 | A | 88 | A | A | A |

TABLE 7-continued

| | | Components of setting gel (g) | | | Physical properties of setting gel | | | | | |
|---|---|---|---|---|---|---|---|---|---|---|
| | Cationic thickener | Distilled water | Ethanol | Polymer for setting | Viscosity (cP) | Trans- parency | Setting property (%) | Feel | Flaking | Facility for shampooing |
| | obtained in Example 23 (3.5) | | | polymer for setting (14) | | | | | | |
| 65 | Cationic thickener obtained in Example 18 (4) | (66) | (10) | Nonionic polymer for setting (20) | 10800 | A | 82 | A | A | A |
| 66 | Cationic thickener obtained in Example 20 (4) | (66) | (10) | Nonionic polymer for setting (20) | 10000 | A | 84 | A | A | A |
| 67 | Cationic thickener obtained in Example 22 (4) | (66) | (10) | Nonionic polymer for setting (20) | 9200 | A | 88 | A | A | A |
| 68 | Cationic thickener obtained in Example 23 (4) | (66) | (10) | Nonionic polymer for setting (20) | 8000 | A | 91 | A | A | A |
| 69 | Cationic thickener obtained in Example 18 (3.5) | (66.5) | (10) | Cationic polymer for setting (14) | 8600 | A | 72 | A | A | A |
| 70 | Cationic thickener obtained in Example 20 (3.5) | (66.5) | (10) | Cationic polymer for setting (14) | 8100 | A | 74 | A | A | A |
| 71 | Cationic thickener obtained in Example 22 (3.5) | (66.5) | (10) | Cationic polymer for setting (14) | 7600 | A | 77 | A | A | A |
| 72 | Cationic thickener obtained in Example 23 (3.5) | (66.5) | (10) | Cationic polymer for setting (14) | 6800 | A | 80 | A | A | A |
| 73 | Cationic thickener obtained in Example 18 (4) | (66) | (10) | Cationic polymer for setting (20) | 8100 | A | 80 | A | A | A |
| 74 | Cationic thickener obtained in Example 20 (4) | (66) | (10) | Cationic polymer for setting (20) | 7600 | A | 80 | A | A | A |
| 75 | Cationic thickener obtained in Example 22 (4) | (66) | (10) | Cationic polymer for setting (20) | 6800 | A | 86 | A | A | A |
| 76 | Cationic thickener obtained in Example 23 (4) | (66) | (10) | Cationic polymer for setting (20) | 5700 | A | 89 | A | A | A |
| 77 | Cationic thickener obtained in Example 18 (3.5) | (66.5) | (10) | Amphoteric polymer for setting (14) | 8900 | A | 79 | A | A | A |
| 78 | Cationic thickener obtained in Example 20 (3.5) | (66.5) | (10) | Amphoteric polymer for setting (14) | 8600 | A | 78 | A | A | A |
| 79 | Cationic thickener obtained in Example 22 (3.5) | (66.5) | (10) | Amphoteric polymer for setting (14) | 8600 | A | 79 | A | A | A |
| 80 | Cationic thickener obtained in Example 23 (3.5) | (66.5) | (10) | Amphoteric polymer for setting (14) | 8100 | A | 81 | A | A | A |
| 81 | Cationic thickener obtained in Example 18 (4) | (66) | (10) | Amphoteric polymer for setting (20) | 8600 | A | 85 | A | A | A |
| 82 | Cationic thickener obtained in Example 20 (4) | (66) | (10) | Amphoteric polymer for setting (20) | 8100 | A | 84 | A | A | A |
| 83 | Cationic thickener obtained in Example 22 (4) | (66) | (10) | Amphoteric polymer for setting (20) | 7600 | A | 85 | A | A | A |
| 84 | Cationic thickener obtained in Example 23 (4) | (66) | (10) | Amphoteric polymer for setting (20) | 6800 | A | 87 | A | A | A |
| 85 | Cationic thickener obtained in Example 31 (4) | (66) | (10) | Nonionic polymer for setting (20) | 11600 | A | 75 | B | B | A |
| 86 | Cationic thickener obtained in Example 31 (4) | (66) | (10) | Cationic polymer for setting (20) | 7800 | A | 79 | B | B | A |
| Comparative Example No. 9 | — | (66) | (10) | Nonionic polymer for setting (20) | 6800 | A | 63 | C | C | A |

From the results shown in Table 7, it can be seen that a gel for hair setting can be prepared even though any of nonionic, cationic and amphoteric polymers for setting is used when the cationic thickener used in Examples 62 to 85 according to the present invention is used, and that the obtained setting gel for hair (cosmetic composition) is excellent in the physical properties such as facility for shampooing and setting property.

In addition to the ingredients used in the Examples, other ingredients can be used in the Examples as set forth in the specification to obtain substantially the same results.

What is claimed is:

1. A cationic thickener having a viscosity of 3,000 to 90,000 cP at 25° C., which forms a gel when dissolved in water, prepared in a nonaqueous solvent system in the absence of water and a surface active agent by polymerizing a monomer composition containing (A) 15 to 85% by weight of at least one of an acrylic monomer having an amino group and a methacrylic monomer having an amino group, represented by the general formula (I):

$$CH_2=C(R^1)-C(=O)-A-B-N(R^2)(R^3) \quad (I)$$

wherein $R^1$ is a hydrogen atom or methyl group, each of $R^2$ and $R^3$ is independently a hydrogen atom, methyl group, ethyl group or t-butyl group, A is oxygen atom or —NH— group, and B is a linear or branched alkylene group having 1 to 4 carbon atoms, (B) 20 to 80% by weight of a vinyl monomer represented by the general formula (II):

$$CH_2=C(R^1)-R^4 \quad (II)$$

wherein $R^1$ is as defined above and $R^4$ is a group represented by the general formula:

$$-N\overbrace{-(CH_2)_p-C(=O)-}$$

wherein p is 3 or 4, or a group represented by the general formula:

$$-C(=O)-NH_2,$$

(C) 2 to 20% by weight of at least one of a monomer having acryloyl group and a monomer having methacryloyl group represented by the general formula (III):

$$CH_2=C(R^1)-C(=O)-A-R^5-R^6 \quad (III)$$

wherein $R^1$ and A are as defined above, $R^5$ is a linear or branched alkylene group having 1 to 17 carbon atoms, a group represented by the general formula (IV):

$$-(C_2H_4O)_q- \quad (IV)$$

wherein q is an integer of 1 to 25 or a group represented by the general formula (V):

$$-(C_3H_6O)_r- \quad (V)$$

wherein r is an integer of 1 to 25, and $R^6$ is hydrogen atom or methyl group, and (D) 0.1 to 20% by weight of a crosslinkable vinyl monomer having at least two carbon-carbon unsaturated bonds.

2. The cationic thickener of claim 1, wherein said "monomer (C) includes a member selected from the group consisting of" stearyl acryloyl and methoxy polyethyleneglycol methacryloyl.

3. The cationic thickener of claim 1, wherein said crosslinkable vinyl monomer is an acrylic monomer having at least 2 carbon-carbon unsaturated double bonds or a methacrylic monomer having at least 2 carbon-carbon unsaturated double bonds.

4. A process for preparing a cationic thickener having a viscosity of 3,000 to 90,000 cP at 25°, which forms a gel when dispersed into water, comprising the steps of:

polymerizing in a nonaqueous solvent system in the absence of water and a surface active agent, a monomer composition comprising (A) 15 to 85% by weight of at least one of an acrylic monomer having an amino group and a methacrylic monomer having an amino group represented by the general formula (I):

$$CH_2=C(R^1)-C(=O)-A-B-N(R^2)(R^3) \quad (I)$$

wherein $R^1$ is a hydrogen atom or methyl group, each of $R^2$ and $R^3$ is independently a hydrogen atom, methyl group, ethyl group or t-butyl group, A is oxygen atom or —NH— group, and B is a linear or branched alkylene group having 1 to 4 carbon atoms, (B) 20 to 80% by weight of a vinyl monomer represented by the general formula (II):

$$CH_2=C(R^1)-R^4 \quad (II)$$

wherein $R^1$ is as defined above and $R^4$ is a group represented by the general formula:

$$-N\overbrace{-(CH_2)_p-C(=O)-}$$

wherein p is 3 or 4, or a group represented by the general formula:

$$-C(=O)-NH_2,$$

(C) 2 to 20% by weight of at least one of a monomer having acryloyl group and a monomer having methacryloyl group represented by the general formula (III):

$$CH_2=C(R^1)-C(=O)-A-R^5-R^6 \quad (III)$$

wherein $R^1$ and A are as defined above, $R_5$ is a linear or branched alkylene group having 1 to 17 carbon atoms, a group represented by the general formula (IV):

$$-(C_2H_4O)_q- \quad (IV)$$

wherein q is an integer of 1 to 25 or a group represented by the general formula (V):

$-(C_3H_6O)_r-$ (V)

wherein r is an integer of 1 to 25, and $R^6$ is hydrogen atom or methyl group, and
(D) 0.1 to 20% by weight of a crosslinkable vinyl monomer having at least two carbon-carbon unsaturated bonds with heating in a nonaqueous solvent under an atmosphere of inert gas, and removing a solvent from an obtained reaction solution to give a powder.

5. The process for preparing a cationic thickener of claim 4, wherein said solvent includes a good solvent selected from the consisting of monohydric alcohols having 1 to 3 carbon atoms, acetone, ethyl acetate, benzene, toluene, and xylene.

6. The process for preparing a cationic thickener of claim 5, wherein said good solvent is a monohydric alcohol having 1 to 3 carbon atoms.

7. The process for preparing a cationic thickener of claim 4, wherein said nonaqueous solvent is a mixture of two solvents.

8. The process for preparing a cationic thickener of claim 7, wherein said mixture is a mixture of a monohydric alcohol having 1 to 3 carbon atoms and a linear, branched or cyclic aliphatic hydrocarbon having at most 15 carbon atoms.

\* \* \* \* \*